United States Patent [19]

Anderson et al.

[11] Patent Number: 4,469,689

[45] Date of Patent: Sep. 4, 1984

[54] SULFONATE CONTAINING ESTER PRODRUGS OF CORTICOSTEROIDS

[75] Inventors: Bradley D. Anderson, Kalamazoo; Robert A. Conradi, Portage, both of Mich.

[73] Assignee: The Upjohn Company, Kalamazoo, Mich.

[21] Appl. No.: 480,603

[22] Filed: Mar. 30, 1983

[51] Int. Cl.$^3$ .............................. A61K 31/56
[52] U.S. Cl. ................. 424/243; 260/397.45
[58] Field of Search .................... 260/397.45

[56] References Cited

U.S. PATENT DOCUMENTS 4,189,477  2/1980  Nedelec et al. ............... 260/397.45
4,296,109  10/1981  Laurent et al. ..................... 424/243

FOREIGN PATENT DOCUMENTS 2325358  11/1973  Fed. Rep. of Germany ...... 424/243
940701  10/1963  United Kingdom ................ 424/243

OTHER PUBLICATIONS

Anderson, B. D. and Taphouse, V., J. Pharm. Sci. 70 (2), Feb. 1981, pp. 181–186, "Initial Rate Studies of Hydrolysis and Acyl Migration in Methylprednisolone 21-Hemisuccinate and 17-Hemisuccinate".

Flynn, G. L. and Lamb, D. J., J. Pharm. Sci. 59 (10), Oct. 1970, pp. 1433–1438, "Factors Influencing Solvolysis of Corticosteroid-21-Phosphate Esters".

Garrett, E. R., J. Pharm. Sci. 51 (5), May 1962, pp. 445–450, "Prediction of Stability in Pharmaceutical Preparations X: Alkaline Hydrolysis of Hydrocortisone Hemisuccinate".

Kawamura, M., et al., Yakugaku Zasshi, 91 (8), 1971, pp. 863–870, "Pharmaceutical Studies on Water-Soluble Corticosteroid Derivatives, II, Stability of Hydrocortisone 21-Aminoalkylcarboxylates in Solution".

Kawamura, M., et al., Yakugaku Zasshi, 91 (8), 1971, pp. 871–878, "Pharmaceutical Studies on Water-Soluble Corticosteroid Derivatives, III, Stability of Hydrocortisone 21-Sulfobenzoates and 21-Sulfate in Solution".

Yamamoto, R., et al., Yakugaku Zasshi, 91 (8), 1971, pp. 855–862, "Pharmaceutical Studies on Water-Soluble Corticosteroid Derivatives, I, Stability of Hydrocortisone 21-Hemiesters in Solution".

*Primary Examiner*—Elbert L. Roberts
*Attorney, Agent, or Firm*—L. Ruth Hattan

[57] ABSTRACT

Novel solution stable ester prodrugs of corticosteroids of the formula

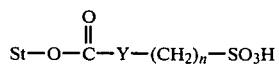

and their salts.

9 Claims, No Drawings

SULFONATE CONTAINING ESTER PRODRUGS OF CORTICOSTEROIDS

BACKGROUND OF THE INVENTION

Conventional anti-inflammatory steroids, such as cortisone, hydrocortisone, prednisone, methylprednisolone, etc., are generally poorly water soluble and therefore not suited for intravenous administration. Several types of soluble C-21 derivatives of such steroids have been disclosed in the patent literature including dicarboxylic acid hemiesters, sulfobenzoates, sulfopropionates, sulfates, phosphates, and aminoalkanoyloxy derivatives. While solubilization can generally be attained quite readily using a variety of such pro-moieties, most of the aforementioned derivatives possess other disadvantages limiting their utility as water soluble prodrugs. The term "prodrug" denotes a derivative of an active drug which is converted after administration back to the active drug. The "pro-moiety" referred to in this application is the fragment attached to the steroid via an ester linkage and removed by ester hydrolysis in vivo. A major problem with many common derivatives is their solution instability. Dicarboxylic acid hemiesters of corticosteroids such as succinate esters, for example, are marketed commercially as lyophilized powders for reconstitution prior to injection due to their solution instability (see, for example, E. R. Garrett, *J. Pharm. Sci.*, 51, 445 (1962); B. D. Anderson and V. Taphouse, *J. Pharm. Sci.*, 70, (1981); R. Yamamoto, S. Fujisawa, and M. Kawamura, *Yakugaku Zasshi*, 91, 855 (1971)). Corticosteroid 21-aminoalkyl carboxylate derivatives reported in the literature also undergo rapid hydrolysis in aqueous solution (M. Kawamura, R. Yamamoto, and S. Fujisawa, *Yakugaku Zasshi*, 91, 863 (1971)).

Certain derivatives which do appear to exhibit better solution stability suffer from other disadvantages. 21-sulfate esters, for example, may not be readily converted to the active parent drug in vivo as suggested by the fact that the 21-sulfate of hydrocortisone is inactive in mice (M. Kawamura, R. Yamamoto, and S. Fujisawa, *Yakugaku Zasshi*, 91, 871 (1971); meta-sulfobenzoate esters which have been reported as having improved solution stability (M. Kawamura, R. Yamamoto and S. Fujisawa, ibid, French Patent Derwent No. 76199 U) are frequently not highly water soluble and thus may have limited utility as injectable prodrugs. Phosphate esters may in some cases possess the requisite solubility, solution stability, and bioconversion rates but exhibit other disadvantages. Several undesirable features of phosphate esters are apparent: (1) Phosphate esters are often difficult to purify and are frequently very hygroscopic. (2) The stability of phosphate esters is optimum above pH 7 where other modes of drug degradation may be a problem. Glass surfaces are also more likely to delaminate in alkaline conditions resulting in particulate problems. (3) Precipitation of free corticosteroid due to the limited amount of hydrolysis which does occur may limit product shelf-life. Solubilization of free corticosteroid due to micelle formation by the intact prodrug is a desirable feature which phosphates esters exhibit to only a limited extent. (4) Concentrated solutions of phosphate esters of corticosteroids exhibit accelerated reaction velocities due to micelle formation, limiting shelf-life in concentrated solutions (G. L. Flynn and D. J. Lamb, *J. Pharm. Sci.*, 1433 (1970)). Sulfopropionate esters of corticosteroids have also been reported as readily water soluble and as having improved solution stability (Derwent Accession No. 27789C.). Sulfoacetate esters are also known (Derwent 9453F). The esters claimed in the present invention are significantly more stable than sulfoacetate or sulfopropionate esters. In addition, it will be shown herein that the esters claimed in the present invention are significantly more bioavailable than the sulfopropionate ester.

FIELD OF INVENTION

The present invention is novel sulfonate containing ester prodrugs of corticosteroids and formulations of steroid prodrugs.

SUMMARY OF INVENTION

The compounds of the present invention are sulfonate containing ester prodrugs of corticosteroids which are solution stable in vitro but are rapidly converted in vivo to the active parent drug and are therefore useful as anti-inflammatory agents. The compounds of the present invention are represented by the following general Formula I and their salts with pharmaceutically acceptable bases:

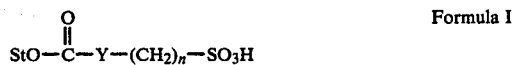

Formula I wherein St represents a corticosteroid moiety bonded to the carbonyl via the 21-hydroxy group of said corticosteroid; Y is a bond, or —O—; and n is an integer of from 5 to 10.

Pharmaceutically acceptable base addition salts of the compounds of Formula I are also a part of the present invention. Any reference herein to the compounds of Formula I is intended to include pharmaceutically acceptable salts thereof. Solution stable formulations of the compounds of Formula I are also a part of the present invention.

DETAILED DESCRIPTION OF INVENTION

In the compounds of general Formula I St represents the parent corticosteroid minus the 21-hydroxyl group of said corticosteroid which is necessary to form the novel esters of the present invention. The parent corticosteroid could be depicted as StOH wherein the OH is located at the 21-position of the corticosteroid which may be depicted as follows:

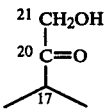

Of course the carbon atoms at positions C-17 and C-21 may be substituted as will be apparent from the description hereinbelow.

The term corticosteroid as used herein is taken to mean not only the steroids produced by the adrenal cortex but also synthetic equivalents, i.e., non-naturally occuring steroids which possess physiological properties characteristic of naturally occurring corticosteroids. Reference is made to *Drill's Pharmacology in Medicine*, McGraw-Hill Book Company, New York, (1965), Chapter 73: Adrenal Cortex and Adrenocortical Hormones, particularly pages 1185-1187 wherein typical corticosteroids employed in the present invention are described. Also, typical corticosteroids represented by StOH include those described in Applezweig, *Steroid Drugs*, McGraw-Hill Book Company, Inc., New York, 1962, pp. 435-731, and in particular the compounds associated with the following parenthetical numbers: 675; 684; 685; 734; 1030; 1033; 1034; 1035; 1036; 1038; 1039; 1048; 1051; 1052; 1059; 1061; 1063; 1064; 1066; 1067; 1068; 1070; 1071; 1072; 1073; 1078; 1080; 1082; 1083; 1084; 1086; 1087; 1088; 1092; 1093; 1094; 1095; 1099; 1100; 1101; 1105; 1107; 1108; 1109; 1110; 1111; 1112; 1116; 1116-A; 1117; 1119; 1120; 1121; 1125; 1128; 1135; 1140; 1141; 1142; 1143; 1149; 1151; 1155; 1168; 1169; 1170; 1172; 1173; 1174; 1175; 1176; 1178; 1181; 1182; 1182-A; 1183; 1184; 1186; 1187; 1189; 1193; 1194; 1197; 1198; 1206; 1207; 1214; 1215; 1216; 1217; 1218; 1220; 1221; 1226; 1227; 1230; 1231; 1242; 1243; 1244; 1246; 1248; 1251; 1270; 1272; 1273; 1274; 1275; 1279; 1280; 1281; 1282; 1283; 1285; 1286; 1287; 1294; 1295; 1296; 1306; 1307; 1308; 1319; 1320; 1322; 1323; 1324; 1325; 1327; 1328; 1329; 1330; 1331; 1333; 1334; 1336; 1337; 1338; 1339; 1340; 1350; 1351; 1352; 1363; 1368; 1370; 1385.

Also, typical corticosteroids represented by StOH include those described in Applezweig, *Steroid Drugs*, Holden-Day, Inc., San Francisco, 1964, pp. 109–438, and in particular the compounds associated with the following "catalogue" numbers: 2680; 2681; 2709; 2713; 2714; 2716; 2717; 2719; 2720; 2722; 2723; 2724; 2725; 2726; 2727; 2728; 2729; 2730; 2731; 2732; 2733; 2734; 2735; 2736; 2737; 2738; 2739; 2740; 2741; 2742; 2743; 2744; 2745; 2746; 2814; 2826; 2827; 3036-A; 3036-B; 3036-C; 3036-D; 3036-E; 3036-F; 3036-G; 3036-H; 3036-I; 3036-J; 3036-K; 3036-L; 3036-M; 3036-N; 3036O; 3036P; 3036-Q; 3036-R; 3036-S; 3036-T; 3036U; 3036-V; 3052; 3054; 3057; 3071; 3073; 3074; 3075; 3078; 3081; 3082; 3087; 3088; 3090; 3108; 3109; 3109-A; 3111; 3112; 3112-A; 3114; 3117; 3118; 3119; 3119A; 3120; 3121; 3122; 3122-A; 3123; 3124; 3130; 3131; 3132; 3133; 3139; 3140; 3141; 3142; 3143; 3143-A; 3145; 3147; 3148; 3151; 3152; 3154; 3168; 3169; 3170; 3171; 3171-A; 3174; 3175; 3175-A; 3178; 3180; 3181; 3182; 3183; 3184; 3184-A; 3189; 3191; 3192; 3193; 3193-A; 3196; 3198; 3199; 3200; 3201; 3202; 3203; 3204; 3205; 3206; 3215; 3216; 3217; 3218; 3220; 3222; 3226; 3227; 3231; 3232; 3232-A; 3234; 3235; 3235-A; 3237; 3238; 3239; 3240; 3241; 3242; 3242-A; 3248; 3249; 3250; 3251; 3251-A; 3253; 3254; 3255; 3256; 3257; 3258; 3259; 3260; 3265; 3266; 3267; 3268; 3269; 3273; 3287; 3288; 3289; 3289-A; 3291; 3292; 3293; 3293-A; 3296; 3297; 3298; 3299; 3300; 3301; 3302; 3303; 3303-A; 3316; 3317; 3318; 3319; 3319-A; 3332; 3333; 3334; 3335; 3337; 3338; 3339; 3340; 3341; 3342; 3343; 3344; 3345; 3346; 3347; 3349; 3350; 3351; 3372; 3373; 3373-B; 3374; 3375; 3376; 3377; 3379.

The corticosteroid field, i.e., the compounds and their use as pharmacologically active agents is well documented, and numerous other references exist which describe the synthesis and use of corticosteroids as depicted above by StOH. Substantially any corticosteroid having a hydroxyl group at the C-21 position of the molecule is useful as the parent steroid in forming the novel esters of the present invention. The compounds of Formulas A and B (see Formula Chart) represent preferred corticosteroids used to contribute the St moiety of the compounds of Formula I. Particularly preferred corticosteroids which are useful in forming the esters of Formula I are the following: hydrocortisone, cortisone, corticosterone, prednisone, prednisolone, 6α-methylprednisolone, triamcinolone, dexamethasone, betamethasone, flumethasone, 11-deoxy corticosterone, flu- prednisolone, 9α-fluorohydrocortisone, flurandrenolone, paramethasone, chlorprednisone, and dehydrocorticosterone. The compounds of Formula I wherein Y is a bond are more preferred.

Illustrative examples of pharmaceutically acceptable base addition salts of the compounds of Formula are alkali metal salts or organic tertiary amine salts as formed by treatment with a suitable base as set forth hereinbelow.

The compounds of Formula I are prodrugs of the corticosteroids represented by the St moiety in said Formula and have the same utility as the known or parent corticosteroid. Thus the compounds of Formula I are useful in treating warm blooded animals, e.g., dogs, cats, monkeys, horses, and particularly humans for various disease conditions. For example, the compounds of Formula I are useful in those situations where one wishes to elicit an anti-inflammatory, anti-pruritic or vasoconstrictive action inherent in the parent corticosteroid. The compounds of the present invention and the compounds utilized in the novel formulations of the present invention are particularly useful in treating acute adrenal insufficiency (Addison's disease); allergic conditions such as asthma, contact dermatitis, serum sickness, angioneurotic edema, drug hypersensitivity reactions and anaphylactoid reactions; collagen and musculoskeletal diseases, such as, rheumatoid arthritis, dermatomyositis, lupus erythematosus, rheumatic fever; dermatological diseases, such as pemphigus and severe erythema multiforme; ulcerative colitis, and acute exacerbations of multiple sclerosis. Also when the parent corticosteroid contributing the St moiety of the compounds of Formula I possesses mineralocorticoid properties said compounds of Formula I are useful particularly in maintaining a physiological electrolyte level in patients with acute adrenal insufficiency.

Although the compounds of Formula I and salts thereof may be administered orally, these compounds are designed for and have their primary application in those situations where oral therapy is not feasible. The compounds of Formula I are best suited for administration as sterile aqueous solutions by intravenous injection, intravenous infusion, or intramuscular or subcutaneous injection, or intravenous bolus.

The novel compounds of the present invention provide marked advantages over known corticosteroids or derivatives thereof in that these novel compounds are highly water soluble and when formulated in a manner which fully exploits the advantageous physicochemical properties of these compounds are sufficiently stable in aqueous solution to afford long term storage of solutions of said novel compounds.

The solution stability of these compounds is due to several features: (1) The derivatives are highly soluble in the pH range 3-6 which is the pH range in which ester hydrolysis in aqueous solution is minimized. (2) The sulfonate group is sufficiently distant from the ester linkage that any catalytic effect or undesirable substituent effect on the ester hydrolysis is minimal. (3) The compounds self-associate in concentrated solutions to form molecular aggregates which increase the shelf life of formulations by (a) retarding hydroxide ion catalyzed ester hydrolysis at high concentrations, and (b) solubilizing any parent corticosteroid present in and resulting from the hydrolysis of a solution of a compound of the present invention.

The solution stability of the compounds of Formula I varies to some extent depending on whether Y is —O—or a bond and on the value for n. From the hydrolysis rate constants determined at 25° C. at various pH vlaues for dilute aqueous solutions of the compounds of the invention, estimates of $t_{90\%}$ (time for 10% hydrolysis) may be calculated. Such values, calculated at the pH of optimum stability, for the compounds of Examples 1 and 2 are listed in Table I. Also included in Table I is the optimum $t_{90\%}$ value, determined in the same way, for the sulfopropionate esters of methylprednisolone, a compound disclosed in the prior art. From these values it is readily apparent that the compounds of the present invention are significantly more stable in dilute aqueous solution than the previously known compound.

TABLE I

| Compound | pH | $t_{90\%}$ (years) |
| --- | --- | --- |
| Example 1 | 4.75 | 2.7 |
| Example 2 | 4.75 | 3.0 |
| Sulfopropionate ester of methylprednisolone | 4.15 | 0.71 |

The actual shelf-life of formulations of the above compounds would be expected to differ fom the above estimates for two reasons: (1) The solubility of the parent corticosteroid formed on hydrolysis may be exceeded prior to 10% degradation of the ester. Micelle formation by the intact prodrugs of Formula I results in solubilization of free corticosteroid thereby prolonging shelf-life. The degree of solubilization varies with the ester concentration, nature of the pro-moiety, and the structure of the corticosteroid. (2) Micelle formation by the intact prodrug in concentrated solutions results in stabilization of the ester linkage toward base catalyzed hydrolysis. For example, the base catalyzed hydrolysis rate in a 0.267 M solution of the compound of Example 1 is less than one-seventh the rate in a $5 \times 10^{-4}$ M solution.

In addition to the effects of formulation concentration, pH and storage temperature have a dramatic impact on the stability of formulations. However, in formulations buffered at a pH at or near the pH-hydrolysis rate minimum (3-6) and stored at room temperature (25° C.), the compounds of the present invention are solution stable for several months, regardless of concentration. The stability or shelf-life of solutions of compounds of the present invention can be prolonged by decreasing the storage temperature, e.g., to temperatures from 4° C. to 24° C.

As indicated previously, the compounds of Formula I exhibit stability in water only when the pH of their solution is properly controlled. Ideally, the pH will be maintained at a level where the hydrolysis of the ester is at a minimum. This minimum depends to a certain degree on the chemical structure of the pro-moiety, the formulation concentration, and the temperature of storage but in general will be at a pH about 3 to 6 for the compounds of this invention. Most advantageously, buffers should be employed to maintain the pH at or near the desired level throughout the shelf life of the formulation. Suitable buffers are those which are physiologically acceptable and exhibit sufficient buffer capacity in the pH range 3-6, e.g., acetate, citrate, succinate, adipate, or phthalate buffers and the like. The quantity of buffer used is determined by means known in the art and will depend on the pH desired, the concentration of the solution, and the buffering capacity of the buffer.

The concentration of the solution stable formulations of the compounds of Formula I depends on the activity level of and the ultimate dose of parent corticosteroid desired. In general the stability of the formulations increases as the concentration of novel ester increases. In essence the solution stable formulations may be as concentrated as viscosity properties permit or until the solubility of the novel ester is exceeded. Inasmuch as the compounds of the present invention are converted to the parent corticosteroid in vivo, ideally the concentration of the novel ester and the volume of the solution administered will be chosen to provide a quantity of parent corticosteroid which is known to be effective. For example, a 0.267M solution of the compound in Example 3, set forth below, is equivalent to 100 mg/ml of 6α-methylprednisolone.

Sterile aqueous solutions of the compounds of Formula I typically will contain other components such as preservatives, anti-oxidants, chelating agents, or other stabilizers. Suitable preservatives can include benyl alcohol, the parabens, benzalkonium chloride, or benzoic acid. Anti-oxidants such as sodium bislufite, ascorbic acid, propyl 3,4,5-trihydroxy benzoate, and the like may be employed. Chelating agents such as citrate, tartrate, or ethylenediaminetetraacetic acid (EDTA) may be used. Other additives useful as stabilizers of corticosteroid prodrugs (e.g., creatinine, polysorbate 80, and the like) may be employed.

Typical formulations useful in practicing the present invention are set forth below.

Since the compounds of Formula I are prodrugs of the parent corticosteroids, their efficacy depends on bioconversion to liberate the free corticoid in vivo. The bioconversion of a compound of Formula I was demonstrated in rats to be quite rapid.

Three Sprague-Dawley rats were surgically prepared by implanting cannulae into the femoral vein and femoral artery. The animals were administered an amount of the compound of Example 1 equivalent to 30mg/kg of methylprednisolone intravenously and 200 μ blood samples were withdrawn at 1, 2, 5, 15, and 45 minutes. The samples were quenched immediately in 3-5ml of 18% MeOH/H$_2$O containing 1% acetic acid and stored over dry ice. The samples were then analyzed for methylprednisolone by HPLC. The blood level of methylprednisolone peaked in 2-5 minutes at a concentration of 16.8±2.0 μg/ml indicating rapid bioconversion to the free corticoid.

In contrast, a similar study in which the sulfopropionate ester of methylprednisolone was injected into two rats at a dose of 30 mg/kg showed peak blood levels of 2.8±0.4 μg/ml occurring at about 15 minutes post injection. Comparing areas under the methylprednisolone concentration vs. time curves (AUC), a measure of total bioavailability, the mean AUC for the compound of Example 1 was 3.6 times greater than that for the sulfopropionate ester. Thus the compounds Formula 1 are demonstrably superior to the sulfopropionate with respect to bioconversion rates and total bioavailability.

The compounds of Formula 1 may be prepared by various means in which the ester moiety is introduced at the 21-position of the steroid by reaction of an appropriate sulfonate compound with the steroid or a 21-substituted derivative of the steroid.

In preparing the compounds of Formula I wherein Y is a bond, equimolar amounts of an intermediate of the formula:

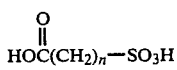

Formula II wherein n is an integer of from 5 to 10, is reacted with a 21-iodo or 21-mesyl derivative of the parent steroid which may be represented respectively by the formulas St-Iodo      Formula III St-O-mesyl      Formula IV wherein St has the meaning defined in Formula I and mesyl means $-S(O_2)-CH_3$. The reaction is carried out in a polar aprotic solvent such as dimethylformamide (DMF), dimethylsulfoxide (DMSO), or tetrahydrofuran (FTHF) in the presence of 2 equivalents of a sterically hindered amine such as diisopropylethylamine or a bicyclic amidine such as 1,8-diazobicyclo[5.4.0]undec-7-ene (DBU)Z. When the 21-iodo steroid derivative is used the reaction proceeds at room temperature, whereas when the 21-mesyl steroid derivative is employed the reaction is heated to about 60°–80° C. When the reaction is complete, the product is isolated by diluting with water, adjusting the pH to ~5, washing with an organic solvent, suitably ethyl acetate, and further purifying by partitioning, crystallization, and/or chromatography.

The compounds of Formula I wherein Y is oxy, i.e., —O—, are prepared by reacting equimolar amounts of an intermediate of the formula

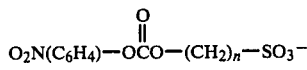

Formula V wherein ($C_6H_4$) is 1,4-phenylene and n is an integer of from 5 to 10 with a parent steroid of the formula StOH wherein St has the meaning defined in Formula I. The reaction is carried out in a dry polar aprotic solvent such as DMF or DMSO in the presence of an acylation catalyst such as dimethylaminopyridine (DMAP) or N-methylimidazole. Although the reaction may be performed at room temperature it is convenient to warm the reaction mixture to about 50°–60° C. with stirring until all of the intermediate of Formula V is consumed. The product is isolated by pouring the reaction mixture into water, maintaining a pH of around 4, and washing with an organic solvent, e.g., ether or ethylacetate. It is then further purified by partitioning, crystallization, and/or chromatography.

To form base addition salts of the compounds of Formula I said compounds are treated with suitable pharmaceutically acceptable inorganic or organic bases by standard procedures. Suitable inorganic bases are, for example, those of alkali metal hydroxides such as sodium and potassium. Suitable organic bases are physiologically acceptable compounds containing tertiary amine functional groups, for example, trialkylamines such as triethylamine.

The compounds of Formula II are prepared by reacting a bromoalkanoate of the formula

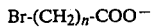      Formula VI wherein n has the meaning defined in Formula I with a molar excess of a sulfite salt in refluxing water or a mixture of water and a water miscible alcohol. The product may be isolated by crystallization or by standard extractive methods. Alternatively the compounds of Formula II may be obtained in two steps by first reacting a terminal olefin of the formula

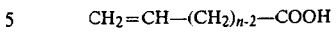      Formula VII wherein n has the meaning defined in Formula I with thiolacetic acid in the presence of ultraviolet radiation or a peroxide catalyst such as dibenzoyl peroxide under an inert atmosphere (e.g., $N_2$) to form a terminal thiolacetate of the formula

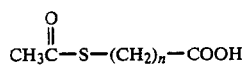      Formula VIII wherein n has the meaning defined in Formula I.

The thiolacetate is isolated by standard methods and is then oxidized by treatment with hydrogen peroxide in acetic acid. The product of oxidation is a sulfoalkanoic acid of Formula II which may be isolated by standard methods.

The compounds of Formula V are prepared by reacting a sulfoalkanol of the formula

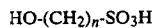      Formula IX wherein n has the meaning defined in Formula I with p-nitrophenylchloroformate in a dry polar aprotic solvent such as DMF or DMSO in the presence of a tertiary amine such as triethylamine. The reaction product is isolated by standard procedures to give a compound of Formula V or is used without isolation to prepare compounds of Formula I.

The compounds of Formula IX may be prepared by reacting an alcohol of the formula

      Formula X wherein n has the meaning defined in formula I and X is Cl, Br, I, $OS(O_2)CH_3$ or $OS(O_2)-(C_6H_4)-CH_3$ with a sulfite salt such as sodium sulfite in a mixture of water and a water miscible alcohol such as ethanol or propanol. The reaction mixture is heated to reflux and when the desired product formation has taken place, the product may be isolated by standard extractive methods and/or by crystallization.

Alternatively the compounds of Formula IX may be synthesized in two steps involving the free radical addition of thiolacetic acid to a compound of the formula

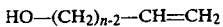      Formula XI wherein n has the meaning defined in Formula I, followed by oxidation of the resulting thiolacetate with hydrogen peroxide in acetic acid to form compounds of Formula IX. The addition reaction is carried out in the presence of ultraviolet radiation or a peroxide catalyst such as dibenzoyl peroxide. The oxidation is carried out in acetic acid to which 90% hydrogen peroxide has been added and is heated to 65°–70° C. The products are isolated by standard methods.

EXAMPLE 1

6α-Methylprednisolone, 21-(6-sulfohexanoate), sodium salt 12.6 g (100 mmol) of $Na_2SO_3$ was combined with 9.75 g (50 mmol) of 6-bromohexanoic acid in 75 ml of water containing 1.92 g (48 mmol of sodium hydroxide. The solution was heated to boiling and allowed to reflux for 24 hours. After cooling, the reaction mixture was adjusted to pH <1 with sulfuric acid and the solution was concentrated to a thick slurry under reduced pressure. The slurry was suspended in hot ethanol and filtered. The filter cake was resuspended in fresh hot ethanol and filtered once more. The combined alcoholic filtrates were concentrated under reduced pressure and the residue was taken up in water and poured through a Dowex ion exchange column (H+ form). Column fractions containing the 6-sulfohexanoic acid product were pooled and concentrated to dryness under reduced pressure.

To form the ester bond at the 21-position of methylprednisolone, 3.3 g (17 mmol) of the product above was combined with 3.62 g (8 mmol) of the 21-mesylate derivative of methylprednisolone in 35 ml of DMF in the presence of 5.9 ml (34 mmol) of diisopropylethylamine. The solution was heated to 80°-90° C. for two days. The reaction mixture was cooled, diluted with 150 ml of 0.1N HCl and extracted with 150 ml of ethylacetate (pH of aqueous phase = 4). The ethylacetate phase was extracted with a second 100 ml of water and the combined aqueous layers were washed with 150 ml of ethylacetate. The aqueous phase was then adjusted to pH 2 with sulfuric acid and extracted three times with 100 ml aliquots of isobutanol. The pooled isobutanol extracts were concentrated under reduced pressure, and the residue was purified by preparative reverse phase liquid chromatography. The chromatographic system consisted of RP-8 bonded-phase silica gel and a mobile phase composed of 30% acetonitrile, 70% water, and 0.1% sodium bisulfate buffer. Column fractions containing the desired compound were pooled and partially concentrated under reduced pressure to remove acetonitrile. The remaining aqueous solution was extracted with two equal volume portions of isobutanol. The isobutanol extracts were concentrated, the residue was taken up in 80% aqueous THF, and the resulting solution was titrated with 1N NaOH to an end point around pH 4. This solution was then concentrated to an oil which was taken up in 20 ml of methanol and added to 200 ml of acetone. After about a 20 minute lag time a solid began to form. The resulting suspension was stirred for 16 hours and then filtered, yielding, after vacuum drying, 1.8 g of white solid.

Elemental analysis: Calculated for $C_{28}H_{39}SO_9Na$: C, 58.52; H, 6.84; S, 5.58; Na, 4.00. Found (corrected for water): C, 58.64; H, 6.83; S, 5.32; Na, 3.92; KF (water)=2.24%. Melting point = 200°-210° C.

UV spectra (in methanol): $\lambda_{max}=243$, $\epsilon_{243}$ (corrected for water) $=1.45\times 10^4$).

EXAMPLE 2

6α-Methylprednisolone, 21-(11-sulfohendecanoate), sodium salt

To a solution of 7.6 g (60 mmol) of sodium sulfite in 38 ml of 1N NaOH, 30 ml water, and 10 ml of n-propanol was added 10.6 g (40 mmol) of 11-bromohendecanoic acid. The reaction mixture was heated to reflux for 8 hours. Upon cooling to room temperature, a small amount of solid precipitated which was removed by filtration and discarded. The solution was then acidified to a pH of less than 1 resulting in copious formation of white crystalline solid. The solid was collected by filtration, washed with a little water, and dried under vacuum to give a 9.2 g yield of the monosodium salt of 11-sulfohendecanoic acid. A portion of this salt dissolved in hot THF/water was converted to the diacid by batchwise treatment with Dowex resin (H+ form).

3.2 (12 mmol) of 11-sulfohendecanoic acid (diacid form) was reacted with 5.43 g (12 mmol) of the 21-mesylate derivative of methylprednisolone in the presence of 4.2 ml (24 mmol) of diisopropylethylamine in 80 ml of DMF. The reaction mixture was briefly heated to over 100° C. then was maintained at 75° C. for about 6 hours. The DMF solution was cooled, diluted with 250 ml of ethylacetate and shaken with 300 ml of water subsequently adjusted to pH 6. The phases were separated, the organic phase was extracted with another 250 ml of water, and the combined aqueous phases were washed with 200 ml of ethylacetate. The aqueous phase was then adjusted to pH 2.3 and extracted with an equal volume of isobutanol. The isobutanol layer was then washed with several equal volume portions of 0.4M sodium phosphate buffer at a pH of about 6. A final wash with sodium phosphate buffer was adjusted to pH 4. The isolated isobutanol phase was then concentrated under reduced pressure and the residue was triturated in about 80 ml of acetone for several hours. Most of the acetone was removed from the suspension by filtration and the remaining slurry was resuspended in 100 ml of ethyl ether. After stirring several hours, the suspension was again filtered and the solid residue was dried under vacuum. 2.4 g of an off-white solid was obtained.

Elemental analysis: Calculated for $C_{33}H_{49}SO_9Na$: C, 61.47; H, 7.66; S, 4.97; Na, 3.57. Found (corrected for water): C, 61.49; H, 7.39; S, 4.78; Na, 3.49.

UV spectra (in methanol): $\alpha_{max}=243$, $\epsilon_{243}$ (corrected for water)$=1.46\times 10^4$ (methylprednisolone $\epsilon_{243}=1.46\times 10^4$. KF (water)=1.82%.

EXAMPLE 3

Dexamethasone, 21-[(6-sulfohexyl)carbonate], sodium salt

To a solution of 6.7 ml (50 mmol) of 1-chloro-6-hydroxyhexane in 30 ml ethanol is added a solution of 9.5 g (75 mmol) of sodium sulfite in 30 ml of water. The resulting solution is heated and allowed to reflux for 2 days. The reaction mixture is then concentrated under reduced pressure and the residue is dissolved in water and passed through a column containing Dowex resin in the H+ form. The effluent fractions containing the desired 1-sulfo-6-hydroxyhexane are then pooled and concentrated to dryness.

A 5.5 g (30 mmol) sample of the sulfo alcohol is then reacted with 6.05 g (30 mmol) of p-nitrophenylchlorocarbonate in the presence of 8.34 ml of triethylamine in 100 ml of dry THF. A precipitate of triethylamine hydrochloride forms immediately. This precipitate is filtered out of solution and the filter cake is washed with dry THF. The filtrate and washings are pooled and 9.8 g (25 mmol) of dexamethasone along with 2.0 ml of pyridine and 1 g of dimethylamino pyridine are added. The reaction mixture is maintained at about 50° C. for one day and is then concentrated under reduced pressure. The residue is taken up in 100 ml dilute phosphate buffer adjusted to pH 7 and is washed with an equal volume of ether. 100 mg of imidazole is added resulting in the rapid and selective hydrolysis of excess p-nitrophenyl ester which is monitored by chromatography. When the p-nitrophenyl ester is consumed the pH is lowered to around 4 and the solution is again washed with ethyl ether. The sodium concentration in the aqueous solution is then increased to around 0.5M by the addition of sodium sulfate and the solution is extracted with isobutanol. The alcohol layer is separated and concentrated under reduced pressure. The residue is then further purified by crystallization and/or chromatography to give the title compound.

EXAMPLE 4

When in the procedure of Example 1 an appropriate amount of the 21-mesylate of triamcinolone, dexamethasone, flumethasone, chlorprednisone, betamethasone, flurandrenolone, prednisone, fluprednisolone, cortisone, corticosterone, 11-deoxycorticosterone, 9α-fluorohydrocortisone, dehydrocorticosterone, or paramethasone is substituted for the 21-mesylate of methylprednisolone the following respective products are obtained as the sodium salt:
triamcinolone, 21-(6-sulfocaproate),
dexamethasone, 21-(6-sulfocaproate),
flumethasone, 21-(6-sulfocaproate),
chlorprednisone, 21-(6-sulfocaproate),
betamethasone, 21-(6-sulfocaproate),
flurandrenolone, 21-(6-sulfocaproate),
prednisone, 21-(6-sulfocaproate),
fluprednisolone, 21-(6-sulfocaproate),
cortisone, 21-(6-sulfocaproate),
corticosterone, 21-(6-sulfocaproate),
11-deoxycorticosterone, 21-(6-sulfocaproate),
9α-fluorohydrocortisone, 21-(6-sulfocaproate),
dehydrocorticosterone, 21-(6-sulfocaproate), and
paramethasone, 21-(6-sulfocaproate).

EXAMPLE 5

When in the procedure of Examples 1 and 2 hydrocortisone 21-iodide is substituted for the 21-mesylate of methylprednisolone the following compounds are obtained:
hydrocortisone, 21-(6-sulfocaproate), sodium salt, and
hydrocortisone, 21-(11-sulfohendecanoate), sodium salt.

The following examples are illustrative of typical formulations of representative compounds of the present invention.

EXAMPLE 6

Hydrocortisone, 21-(6-sulfocaproate), sodium salt (equivalent to 100 mg hydrocortisone): 155 mg
Dilute NaOH to adjust pH to 5.3
Sterile water for injection to make 1 ml

EXAMPLE 7

Methylprednisolone, 21-(6-sulfocaproate), sodium salt (equivalent to 100 mg methylprednisolone): 153 mg
Adipic acid: 7.3 mg
Methyl paraben: 1.5 mg
Propyl paraben: 0.2 mg
NaOh (dilute) to adjust pH to 5.4
Sterile water for injection to make 1 ml

EXAMPLE 8

Dexamethasone, 21-[(5-sulfohexyl)carbonate], sodium salt (equivalent to 20 mg dexamethasone): 166 mg
Creatine: 8.0 mg
Acetic acid: 4.6 mg
Sodium acetate: 2.0 mg
Sodium bisulfite: 1.0 mg
Disodium edetate: 0.5 mg
Benzyl alcohol: 8.8 mg
HCl (dilute) or NaOH (dilute) to adjust pH to 5.0

Water for injection to make 1 ml

FORMULA CHART

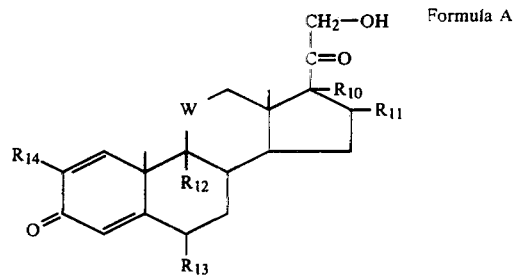

Formula A

In the above Formula A:

W is $-\overset{O}{\underset{\|}{C}}-$, $-\overset{OH}{\underset{|}{CH}}-$, $-\overset{Cl}{\underset{|}{CH}}-$;
$R_{10}$ is H, α-OH;
$R_{11}$ is H, α-CH$_3$, β-CH$_3$, α-F, β-F, α-OH or =CH$_2$;
$R_{12}$ is H, F, Cl, Br;
$R_{13}$ is H, α-F, α-CH$_3$, β-CH$_3$, α-Cl, β-Cl, β-OH;
$R_{14}$ is H$_3$CH$_3$.

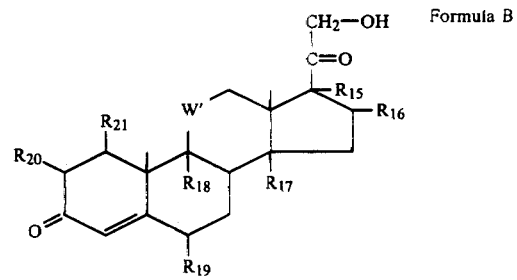

Formula B

In the above Formula B:

W' is $-\overset{O}{\underset{\|}{C}}-$, $-\overset{OH}{\underset{|}{CH}}-$, $-CH_2$, or $-\overset{Cl}{\underset{|}{CH}}-$;
$R_{15}$ is H, α-OH, α-CH$_3$;
$R_{16}$ is H, α-OH, α-CH$_3$;
$R_{17}$ is H, α-OH;
$R_{18}$ is H, α-F, β-F, α-Br, α-Cl, α-OH;
$R_{19}$ is H, β-OH, α-CH$_3$, β-CH$_3$, α-F, α-Cl,
$R_{20}$ is H, α-F, Cl, α-CH$_3$, =CH$_2$;
$R_{21}$ is H, α-OH; with the proviso that one of $R_{20}$ and $R_{21}$ is
hydrogen; preferably $R_{17}$, $R_{20}$ and $R_{21}$ are hydrogen.

We claim:

1. A compound of the formula

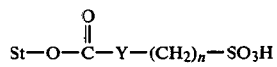

wherein St is corticosteroid absent the C-21 hydroxyl of said corticosteroid; Y is a bond or oxo; and n is an integer of from 5 to 10.

2. A compound of claim 1 wherein Y is a bond.

3. A compound of claim 1 wherein the corticosteroid forming the St moiety is 6α-methylprednisolone, hydrocortisone, corticosterone, prednisone, prednisolone, triamcinolone, dexamethasone, betamethasone, flumethasone, 11-deoxycorticosterone, fluprednisolone, 9α-fluorohydrocortisone, paramethasone, chlorprednisone or dehydrocorticosterone.

4. A compound of claim 3 which is 21-(6-sulfohexanoate)-6α-methylprednisolone sodium salt.

5. A compound of claim 3 which is 21-(11-sulfohendecanoate)-6α-methylprednisolone sodium salt.

6. A compound of claim 3 which is 21-[(6-sulfohexyl)carbonate] dexamethasone sodium salt.

7. A pharmaceutical composition comprising an effective quantity of a compound of claim 1 as a sterile aqueous solution.

8. A composition of claim 7 which is in unit dosage form.

9. A composition of claim 8 wherein the compound is:
21-(6-sulfohexanoate)-6α-methylprednisolone sodium salt,
21-(11-sulfohendecanoate)-6α-methylprednisolone sodium salt, or
21-[(6-sulfohexyl)carbonate]dexamethasone sodium salt.

* * * * *